(12) United States Patent
    Chen

(10) Patent No.: US 10,751,399 B2
(45) Date of Patent: Aug. 25, 2020

(54) CHIMERIC ANTIGEN RECEPTORS THAT BIND TO SSEA4 AND USES THEREOF

(71) Applicant: CHO Pharma USA, Inc., Woburn, MA (US)

(72) Inventor: Lan Bo Chen, Lexington, MA (US)

(73) Assignee: CHO Pharma USA, Inc., Woburn, MA (US)

( * ) Notice: Subject to any disclaimer, the term of this patent is extended or adjusted under 35 U.S.C. 154(b) by 0 days.

(21) Appl. No.: 15/926,382

(22) Filed: Mar. 20, 2018

(65) Prior Publication Data

US 2019/0290744 A1 Sep. 26, 2019

(51) Int. Cl.
```
A61K 39/00      (2006.01)
C07K 14/705     (2006.01)
C07K 16/18      (2006.01)
C07K 14/725     (2006.01)
C07K 14/71      (2006.01)
A61P 35/00      (2006.01)
```
(52) U.S. Cl.
CPC .......... *A61K 39/0011* (2013.01); *A61P 35/00* (2018.01); *C07K 14/7051* (2013.01); *C07K 14/70517* (2013.01); *C07K 14/70578* (2013.01); *C07K 14/71* (2013.01); *C07K 16/18* (2013.01); *A61K 2039/5156* (2013.01); *A61K 2039/5158* (2013.01); *C07K 2317/622* (2013.01); *C07K 2319/00* (2013.01)

(58) Field of Classification Search
CPC .................. A61K 39/0011; C07K 14/7051
See application file for complete search history.

(56) References Cited

U.S. PATENT DOCUMENTS

| | | |
|---|---|---|
| 2014/0271635 A1 | 9/2014 | Brogdon et al. |
| 2016/0102151 A1 | 4/2016 | Wong et al. |
| 2016/0185861 A1 | 6/2016 | Bedoya et al. |
| 2017/0283489 A1 | 10/2017 | Bosio et al. |
| 2018/0028633 A1 | 2/2018 | Chen |

FOREIGN PATENT DOCUMENTS

| | | |
|---|---|---|
| CN | 107188968 A | 9/2017 |
| WO | WO-2016/026742 A1 | 2/2016 |

OTHER PUBLICATIONS

Maher et al Curr Gene Ther. 14(1):35-43 (Year: 2014).*
Yan et al Onco Targets and Therapy 12 193-204 (Year: 2019).*
Kim et al BMB Rep. 50(6): 285-298 (Year: 2017).*
Wang et al Journal of Cancer vol. 10, 3112-3123 (Year: 2019).*
Harichandan et al Journal of Molecular Cell Biology 5, 351-353 (Year: 2013).*
Dai et al "Chimeric Antigen Receptors Modified T-Cells for Cancer Therapy" Journal of the National Cancer Institute vol. 108, pp. 1-14, 2016.
Han et al "Chimeric Antigen Receptor-Engineered T Cells for Cancer Immunotherapy: Progress and Challenges" Journal of Hematology and Oncology vol. 6, pp. 1-7, 2013.
He et al "Knock-In of Large Reporter Genes in Human Cells via CRISPR/Cas9-Induced Homology-Dependent and Independent DNA Repair" Nucleic Acids Research vol. 44, pp. 1-14, 2016.
Jin et al "Safe Engineering of CAR T Cells for Adoptive Cell Therapy of Cancer Using Long-Term Episomal Gene Transfer" Molecular Medicine vol. 8, pp. 702-711, 2016.
Kaiser et al "Towards a Commercial Process for the Manufacture of Genetically Modified T Cells for Therapy" Cancer Gene Therapy vol. 22, pp. 72-78, 2015.
Liechtenstein et al "Lentiviral Vectors for Cancer Immunotherapy and Clinical Applications" Cancers vol. 5, pp. 815-837, 2013.
Maiti et al "Sleeping Beauty System to Redirect T-Cell Specificity for Human Applications" Journal of Immunotherapy, 2013.
Miura et al "Easi-CRISPR for Creating Knock-In and Conditional Knockout Mouse Models Using Long ssDNA Donors" Nature Protocols vol. 13, pp. 195-215, 2018.
Nakazawa et al "PiggyBac-Mediated Cancer Immunotherapy Using EBV-Specific Cytotoxic T-Cells Expressing HER2-Specific Chimeric Antigen Receptor" Molecular Therapy vol. 19, pp. 2133-2143, 2011.
Schonfeld et al "Selective Inhibition of Tumor Growth by Clonal NK Cells Expressing an ErbB2/HER2-Specific Chimeric Antigen Receptor" Molecular Therapy vol. 23, pp. 330-338, 2015.
Lou et al "Stage-Specific Embryonic Antigen-4 as a Potential Therapeutic Target in Glioblastoma Multiforme and Other Cancers" PNAS vol. 111, pp. 2482-2487, 2014.
Pfeifer et al "Sialyl Glycolipid Stage-Specific Embryonic Antigen 4 (SSEA4)—A Novel Target for CAR T Cell Therapy of Solid Cancers" Molecular Therapy vol. 24, p. S259, 2016.
Sivasubramaniyan et al "Expression of Stage-Specific Embryonic Antigen-4 (SSEA-4) Defines Spontaneous Loss of Epithelial Phenotype in Human Solid Tumor Cells" Glycobiology vol. 25, pp. 902-917, 2015.

* cited by examiner

*Primary Examiner* — Anoop K Singh
(74) *Attorney, Agent, or Firm* — Cesari & McKenna, LLP

(57) ABSTRACT

An isolated nucleic acid that contains a nucleotide sequence that encodes the polypeptide of SEQ ID NO: 3. The polypeptide of SEQ ID NO: 3 specifically binds to stage-specific embryonic antigen 4 (SSEA4). Also disclosed is a recombinant cell comprising the isolated nucleic acid described above, a viral vector containing the above isolated nucleic acid, and an isolated polypeptide including the sequence of SEQ ID NO: 3. Provided as well is a chimeric antigen receptor (CAR) that includes a single chain Fv having the sequence of SEQ ID NO: 3 and specifically binding to SSEA4. Moreover, a method is disclosed for treating a tumor by transducing in vitro the T cells of a subject having a tumor expressing SSEA4 with a vector that encodes the CAR, expanding the transduced T cells, and infusing the expanded transduced T cells into the subject, whereby an anti-tumor T cell response is raised.

10 Claims, 2 Drawing Sheets

Specification includes a Sequence Listing.

CHIMERIC ANTIGEN RECEPTORS THAT BIND TO SSEA4 AND USES THEREOF

BACKGROUND

Targeted cancer immunotherapy, as compared to chemotherapy, holds the promise of not only better efficacy, both short-term and long-term, but also fewer side effects.

For example, anti-cancer vaccines targeting a tumor-specific carbohydrate antigen, e.g., Globo H, stage-specific embryonic antigen 3 ("SSEA3"), and stage-specific embryonic antigen 4 ("SSEA4") have been developed to stimulate a patient's own immune system to develop antibodies against these antigens, which leads to antibody-dependent cellular cytotoxicity, antibody-dependent phagocytosis, complement-dependent cell lysis, as well as direct cytostatic and/or cytotoxic effects.

Such an approach often loses effectiveness over time as a result of an inhibitory environment in the tumor. The inhibitory environment blocks one or all of antibodies, NK cells, macrophages, and complement from entering the tumor.

Recently, chimeric antigen receptors ("CARs") have been developed to obviate the drawbacks mentioned above. A CAR contains (i) an extracellular domain that binds to the tumor antigen and (ii) one or more intracellular domains that provide both primary and co-stimulatory signals to the T cells. T cells can be engineered in vitro to express CAR having an extracellular domain of choice.

The CAR approach has proven to be effective, yet not without serious side effects. For example, activation of a large number of T cells expressing CAR causes cytokine release syndrome. This syndrome, characterized by high fever, hypotension, and hypoxia, can result in multi-organ failure and even death.

There is a need to develop CAR-based tumor therapies that are safer and more effective than those currently in use.

SUMMARY

To meet the need discussed above, an isolated nucleic acid is disclosed that contains a nucleotide sequence that encodes the polypeptide of SEQ ID NO: 3. The polypeptide of SEQ ID NO: 3 specifically binds to stage-specific embryonic antigen 4 (SSEA4).

Also disclosed is a recombinant cell comprising the isolated nucleic acid described above, where the recombinant cell expresses the polypeptide of SEQ ID NO: 2.

Further, a viral vector containing the above isolated nucleic acid is within the scope of the invention. The viral vector is a lentiviral vector, a gamma-retroviral vector, or an adeno-associated viral vector.

Moreover, an isolated polypeptide including the sequence of SEQ ID NO: 3 is provided. Again, the isolated polypeptide specifically binds to SSEA4.

Provided as well is a chimeric antigen receptor (CAR) that includes a single chain Fv (scFv) having the sequence of SEQ ID NO: 3 and specifically binding to SSEA4, and a first endodomain from CD3ζ or FcεRIγ.

Finally, a method is disclosed for treating a tumor in a subject, the method including the steps of (i) obtaining T cells from a subject having a tumor; (ii) transducing the T cells in vitro with a vector that contains a nucleic acid encoding a CAR including a scFv that specifically recognizes SSEA-4, whereby the transduced T cells express the CAR; (iii) expanding the transduced T cells in vitro; and (iv) infusing the expanded transduced T cells into the subject having a tumor, whereby an anti-tumor T cell response is raised. The scFv has the amino acid sequence of SEQ ID NO: 3 and cells in the tumor express SSEA4.

The details of one or more embodiments of the invention are set forth in the description and drawings below. Other features, objects, and advantages of the invention will be apparent from the description and from the claims.

BRIEF DESCRIPTION OF THE DRAWINGS

The description below refers to the accompanying drawings, of which.

DETAILED DESCRIPTION

Figure 1:
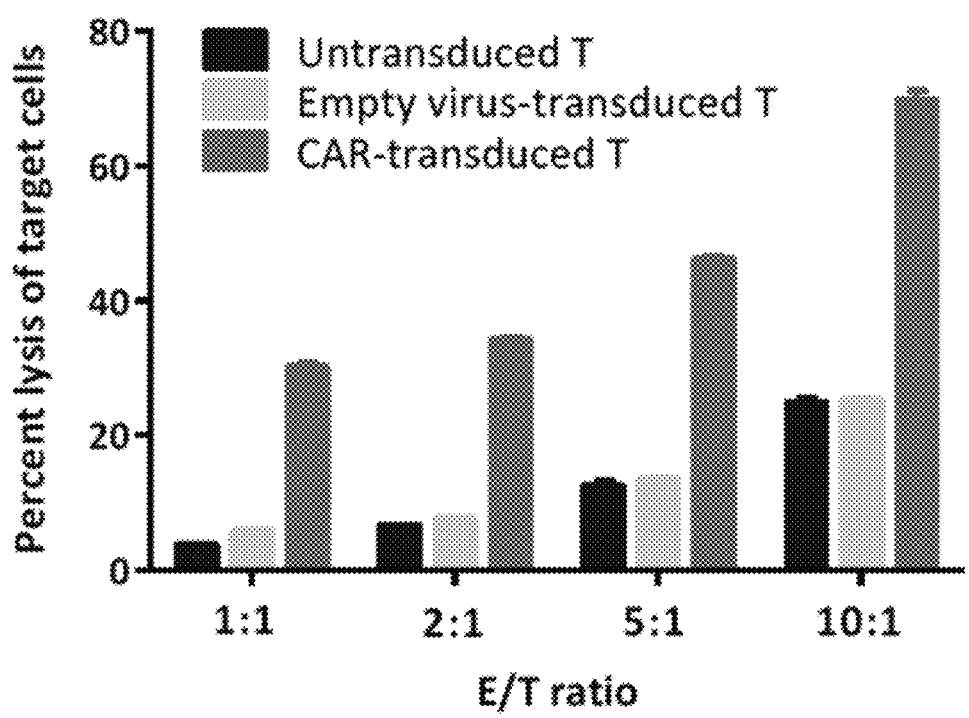
FIG. 1 is a bar graph of percent lysis of target cells by the indicated effector T cells at different effector to target ratios.

As mentioned above, to meet the need to develop CAR-based tumor therapies, an isolated nucleic acid is provided that includes a nucleotide sequence encoding the polypeptide of SEQ ID NO: 3. The polypeptide of SEQ ID NO: 3 is an scFv that specifically binds to SSEA4. In a particular example, the isolated nucleic acid has the nucleotide sequence of SEQ ID NO: 1.

Also within the scope of the invention is a recombinant cell that contains the isolated nucleic acid having the nucleotide sequence of SEQ ID NO: 1. The recombinant cell expresses the polypeptide of SEQ ID NO: 2, i.e., a CAR construct that includes the scFv of SEQ ID NO: 3. The recombinant cell can be a T cell, e.g., a $CD4^+$ or $CD8^+$ T cell. Other cells that can be used include NK, iNKT, monocytes, macrophages, microglia, dendritic cells, and neutrophils.

The isolated nucleic acid that includes a nucleotide sequence encoding the polypeptide of SEQ ID NO: 3, e.g., a CAR construct, can be contained within a viral vector.

Exemplary viral vectors include a lentiviral vector, a gamma-retroviral vector, and an adeno-associated viral vector. Viral vectors based on lentivirus or gamma retroviruses are set forth in Dai et al. 2016, J. Natl. Cancer Inst. 108:1-14 ("Dai et al."); Jin et al. 2016, EMBO Mol. Med. 8:702-711; Liechtenstein et al. 2013, Cancers 5:815-837; and Schonfeld et al. 2015, Mol. Therapy 23:330-338. Such viral vectors are used for integrating the CAR-encoding nucleic acid into T cell genomic DNA to produce stable expression of the CAR.

In a particular example, the viral vector is a lentiviral vector that includes the nucleotide sequence of SEQ ID NO: 1.

Alternatively, the CAR construct can be included in a vector that contains sequences to facilitate transposon-mediated genomic integration into T cells of the CAR-encoding nucleic acid, e.g., SEQ ID NO: 1. Examples of these expression vectors are the so-called "PiggyBac" and "Sleeping Beauty" expression vectors. See Nakazawa et al. 2011, Mol. Ther. 19:2133-2143 and Maiti et al. 2013, J. Immunotherapy 36:112-123.

In yet another alternative, a vector containing the CAR construct also contains genomic nucleic acid sequences flanking the CAR construct that allow for clustered regularly interspaced short palindromic repeat (CRISPR)-mediated insertion of the CAR construct into the genome of the T cells. Examples of CRISPR constructs for inserting the CAR into the genome can be found, e.g., in Miura et al. 2018, Nature Protocols 13:195-215 and He et al. 2016, Nucl. Acids Res. 44:1-14.

Further disclosed is an isolated polypeptide containing the sequence of SEQ ID NO: 3. The isolated polypeptide, an scFv, specifically binds to SSEA-4.

Additionally provided is a CAR that includes an scFv that specifically binds to stage-specific embryonic antigen 4. The scFv can have the sequence of SEQ ID NO: 3. The CAR further includes a first endodomain from CD3ζ or FcεRIγ. In an exemplary CAR, the first endodomain is from CD3ζ

The CAR can also contain a second endodomain. The second endodomain can be, but is not limited to, an endodomain from CD28, CD137, CD4, OX40, and ICOS. If a second endodomain is present in the CAR, the scFv is fused to the second endodomain and the second endodomain is fused to the first endodomain. A particular example of a CAR has a second endodomain from CD137. In another specific example, the CAR has the amino acid sequence of SEQ ID NO: 4.

As mentioned above, a tumor-treating method is provided including, among others, the step of obtaining T cells from a subject having a tumor and the step of transducing the T cells in vitro with a vector that contains a nucleic acid encoding a CAR including a scFv that specifically recognizes SSEA4.

Procedures for obtaining T cells are known in the art. See, e.g., Kaiser et al. 2015, Cancer Gene Therapy 22:72-78 ("Kaiser et al."). The T cells can be $CD4^+$, $CD8^+$, or NK cells. In an exemplary method, $CD8^+$ cells are obtained from the subject.

The T cells are transduced in vitro with the CAR vector described above. Transduction of T cells can be performed by electroporation, lipofection, lentiviral infection, gamma retrovirus infection, or adeno-associated virus infection, depending upon the type of CAR vector employed.

More specifically, if the CAR vector is a PiggyBac, Sleeping Beauty, or CRISPR-based expression vector, it can be transduced into the T cells via electroporation or lipofection. A CRISPR-base expression vector is co-transfected with a vector that expresses a guide RNA complementary to a sequence adjacent to a protospacer adjacent motif at an intended genomic insertion site in the T cells.

If the CAR vector is viral-based, virus particles are prepared and used to infect T cells.

The tumor treatment method also includes the step of expanding the transduced T cells in vitro and the step of infusing the expanded transduced T cells into the subject having a tumor.

Transduced T cells are expanded in vitro, using methods known in the art. See Kaiser et al. The expanded T cells are then infused in one batch or in two or more batches into the subject having a tumor.

In a specific alternative of the tumor-treating method, the method further includes a preconditioning step that is performed prior to the just-mentioned infusion step. The preconditioning step is accomplished by treating the subject with a drug that induces lymphodepletion. Examples of these drugs include cyclophosphamide and fludarabine. Additional drug examples can be found in Dai et al. and Han et al. 2013, J. Hematol. Oncol. 6:47-53.

In the tumor-treating method, the transduced T cells can further express the polypeptide of SEQ ID NO: 5, i.e., an epidermal growth factor receptor t domain III-IV (EGFRt), in addition to the CAR. In this way, the infused expanded T cells can be deleted in vivo with an anti-epidermal growth factor receptor antibody that binds to EGFRt. For example, cetuximab is administered to the subject to kill infused T cells in vivo. An exemplary nucleic acid that encodes the CAR together with EGFRt has the nucleic acid sequence of SEQ ID NO: 1.

The method set forth above can be used for treating a tumor that contains cells expressing SSEA4. The tumors that can be treated include, but are not limited to, breast, colon, gastrointestinal, kidney, lung, liver, ovarian, pancreatic, rectal, stomach, testicular, thymic, cervical, prostate, bladder, skin, nasopharyngeal, esophageal, oral, head and neck, bone, cartilage, muscle, lymph node, bone marrow, and brain tumors.

Without further elaboration, it is believed that one skilled in the art can, based on the disclosure herein, utilize the present disclosure to its fullest extent. The following specific examples are, therefore, to be construed as merely descriptive, and not limitative of the remainder of the disclosure in any way whatsoever. All publications and patent documents cited herein are incorporated by reference in their entirety.

EXAMPLES

Example 1: Production of a Lentivirus Containing an Anti-SSEA4 CAR Construct Construction of Lentiviral Vector Encoding an Anti-SSEA4 CAR A lentiviral construct was prepared in *E. coli* using standard recombinant DNA techniques and verified by DNA sequencing. More specifically, a nucleic acid encoding an scFv having the sequence of SEQ ID NO: 3 was cloned into a lentiviral plasmid vector downstream of an EF-1 alpha promoter and a signal peptide encoding sequence and upstream of a CD8 hinge-encoding sequence to create a CAR cassette. The CAR cassette also encodes a CD8 transmembrane domain, a CD137 intracellular signaling domain, a CD3ζ endodomain, a Thosea asigna self-cleaving peptide T2A, and an EGFRt domain III-IV. The CAR cassette has the nucleic acid sequence of SEQ ID NO: 1. The lentiviral plasmid vector contains additional sequences to facilitate production of lentivirus particles.

Lentivirus Packaging and Production

Packaging and production of lentiviruses was performed using established techniques. Packaging cells, i.e., 293T cells, were plated at $5 \times 10^6$ cells in 10 mL of a complete culture medium in a 10 cm culture dish. The cells were incubated overnight at 37° C. in 5% $CO_2$. A transfection complex was prepared by combining in PBS a transfection reagent, the lentiviral vector described above, a packaging vector, and an envelope vector. The transfection complex was added to the culture dish containing the packaging cells and the cells incubated for 6 to 8 h at 37° C. in 5% $CO_2$. The medium was replaced and the cells incubated for 24 h. The culture medium was collected and replaced with fresh medium. This 24 h incubation and medium collection was repeated twice. All of the collected medium was combined and passed through a 0.45 μm filter. The filtrate was centrifuged at 50,000×g for 2 h to pellet the lentivirus particles. Lentiviral stocks were suspended in PBS and stored at −80° C.

Lentivirus Titration

Lentivirus titers were determined by measuring the amount of lentiviral DNA integrated into the genome of infected cells. 293T cells were plated in 24-well plates at a density of 50,000 cells/well and incubated overnight. Concentrated lentivirus stocks were added to each well together with polybrene to a concentration of 6 μg/mL. The plate was centrifuged briefly and then placed in an incubator at 37° C. with 5% $CO_2$ for 72 hours. Genomic DNA from the lentivirus-transduced cells was extracted with a commercial kit.

Real-time quantitative PCR (RT-QPCR) was used to determine the copy number of lentiviral DNA present in the extracted genomic DNA. The albumin gene was also measured to normalize the results. The primers and probes used for RT-QPCR are shown in Table 1 below.

TABLE 1

RT-QPCR primers and probes

| Primer | Sequence (fluorescent labels) | SEQ ID NO. |
|---|---|---|
| LTR F[a] | TGACAGCCGCCTAGCATTTC | 6 |
| LTR R[a] | GCTCGATATCAGCAGTTCTTGAAG | 7 |
| LTR Probe[a] | CACGTGGCCCGAGAGCTGCATC (5'-FAM-BHQ1-3') | 8 |
| ALB F[b] | GCTGTCATCTCTTGTGGGCTGT | 9 |
| ALB R[b] | ACTCATGGGAGCTGCTGGTTC | 10 |
| ALB Probe[b] | CCTGTCATGCCCACACAAATCTCTCC (5'-FAM-BHQ1-3') | 11 |

[a]LTR = long terminal repeat. These primers specifically amplify lentiviral sequences.
[b]ALB = albumin. These primers specifically amplify the albumin gene Standard curves were constructed by amplifying known amounts of plasmid DNAs carrying the albumin or LTR gene sequences using the RT-QPCR primers described above. The copy number of lentiviral DNA in the genomic DNA was calculated as the ratio of the quantity of LTR sequences divided by the quantity of albumin sequences.

The lentivirus titer was then calculated using the following formula:

$$\text{Lentivirus titer} = \frac{\text{number of cells plated} \times \text{number of copies of lentivirus per cell}}{\text{volume of lentivirus stock added}}$$

An exemplary lentivirus preparation contained $2.6 \times 10^8$ transducing units/mL

Example 2: Preparation of Anti-SSEA4 CAR T Cells

T cells expressing anti-SSEA4 CAR were produced using established techniques. First, peripheral blood mononuclear cells (PBMC) were isolated from whole blood with standard blood separation tubes and the cells re-suspended in complete culture medium. T cells were isolated from the PBMC using a standard magnetic bead separation technique.

The isolated T cells were dispensed into a tissue culture plate and growth media supplemented with 200 IU/mL IL2, 10 ng/mL IL7, 5 ng/mL IL15, and 5 ng/mL IL21 was added such that the cell density was $0.5 \times 10^6$ to $1 \times 10^6$ cells/mL. The plate was incubated at 37° C. in 5% $CO_2$ for 3 days. A lentivirus preparation produced as described above in Example 1 was added to the T cells, and polybrene was also added to a final concentration of 6 µg/ml. The plate was centrifuged at 800×g for 1 hour at room temperature, and then incubated for 5 days at 37° C. in 5% $CO_2$. During the 5 day incubation, the T cells were maintained at a cell density of $0.5 \times 10^6$ cells/mL. The percentage of T cells expressing the anti-SSEA4 CAR was determined by fluorescence-activated cell sorting using an antibody against the EGFR domain III-IV.

In an exemplary preparation, 45.7% of T cells expressed the anti-SSEA4 CAR.

Example 3: Lysis of MCF-7 Target Cells by Anti-SSEA4 CAR T Effector Cells

The ability of anti-SSEA4 CAR T cells to lyse target cells was assessed by a co-culture assay. MCF-7 breast cancer cells, which express SSEA-4, were used as the target cells. 100 µL of MCF-7 target cells at $5 \times 10^5$ cells/mL were transferred into each well of a 96-well plate and cultured overnight at 37° C. in 5% $CO_2$. Effector cells, i.e., anti-SSEA4 CAR T cells, untransduced T cells, and T cells transduced with a negative control lentivirus, were each suspended in serum-free RPMI1640 medium. The culture medium from the 96 well plate was removed and the target cells washed once with PBS. T cells were added into separate wells at effector to target (E/T) ratios of 1:1, 2:1, 5:1 and 10:1. The final volume of medium in each well was adjusted to 100 µL/well using RPMI1640. The co-culture was incubated for 6 h at 37° C. in 5% $CO_2$.

A commercial kit (CytoTox 96® non-radioactive cytotoxicity assay; Promega, WI USA) was used to measure lysis of the target MCF-7 cells by determining the level of lactate dehydrogenase (LDH) released from these cells upon lysis. After co-culturing, the 96-well plate was centrifuged at 1200×g for 5 min. at room temperature, and 50 µL of supernatant from each well was transferred to a new 96 well plate. The LDH level in each supernatant was determined as directed by the manufacturer. Certain wells containing only target cells were treated with a lysis buffer before the centrifugation step. The supernatants from these wells were used to determine the maximum amount of LDH released by the MCF-7 cells. The results are presented in FIG. 1.

The data shows that anti-SSEA4 CAR-T cells lysed significantly more target MCF-7 cells at all E/T ratios, as compared to untransduced T cells and empty lentivirus transduced T cells.

Example 4: Cytokine Release by Anti-SSEA4 CAR-T Cells

Figure 2A:
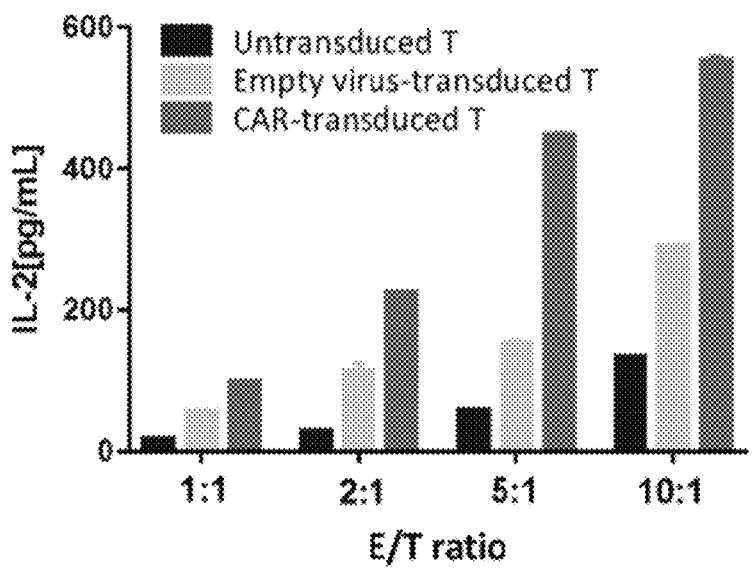
FIG. 2A is a bar graph showing the amount of IL-2 released by the indicated effector T cells after coculturing them with target MCF-7 cells at different effector to target ratios.
Figure 2B:
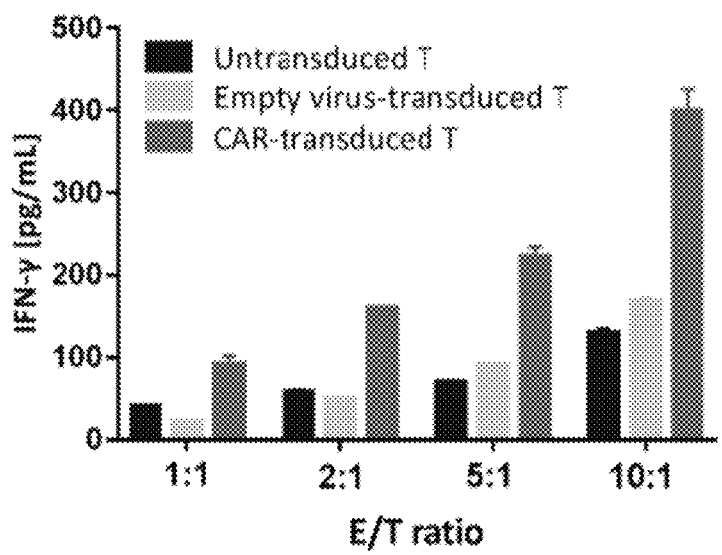
FIG. 2B is a bar graph showing the amount of IFN-γ released by the indicated effector T cells after coculturing them with target MCF-7 cells at different effector to target ratios.

The CAR-T cells described above were co-cultured with target cell line MCF7 in 96-well plates at different E/T ratio for 24 hours in RPMI1640 medium supplemented with 10% FBS in 5% $CO_2$ at 37° C. Culture media was harvested to measure cytokine release by the CAR-T cells. Briefly, the 96-well plate was centrifuged at 1200×g for 5 min. at room temperature, after which 50 µL of supernatant from each well was transferred into a new 96 well plate. The concentration of cytokines IL-2 and IFN-γ was determined using a commercial ELISA kit according to the manufacturer's instructions. The results are shown in FIGS. 2A and 2B. The data shows that SSEA4-specific CAR-T cells robustly secreted both IL-2 and IFN-γ after engaging target tumor cells and this secretion level was significantly greater than either untransduced T cells or T cells transduced with a lentivirus lacking the CAR construct.

Other Embodiments

All of the features disclosed in this specification may be combined in any combination. Each feature disclosed in this specification may be replaced by an alternative feature serving the same, equivalent, or similar purpose. Unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. An isolated nucleic acid, comprising a nucleotide sequence that encodes the polypeptide as set forth in SEQ ID NO: 3.

2. The isolated nucleic acid of claim 1, wherein the nucleotide sequence is SEQ ID NO: 1.

3. An isolated recombinant cell comprising the isolated nucleic acid of claim 2, wherein the isolated recombinant cell expresses the polypeptide of SEQ ID NO: 2.

4. The isolated recombinant cell of claim 3, wherein the cell is a T cell.

5. A viral vector comprising the isolated nucleic acid of claim 1.

6. The viral vector of claim 5, wherein the nucleotide sequence is SEQ ID NO: 1.

7. A method for treating a tumor in a subject, the method comprising:
(i) obtaining T cells from a subject having a breast tumor;
(ii) transducing the T cells in vitro with a vector comprising a nucleic acid encoding a chimeric antigen receptor (CAR) comprising the amino acid sequence as set forth in SEQ ID NO: 3 that specifically recognizes stage-specific embryonic antigen 4 (SSEA4), whereby the transduced T cells express the CAR;
(iii) expanding the transduced T cells expressing the CAR in vitro; and
(iv) infusing the expanded transduced T cells expressing the CAR into the subject having the breast tumor, thereby eliciting an anti-tumor T cell response, wherein cells in the breast tumor express SSEA4.

8. The method of claim 7, wherein the CAR has the amino acid sequence as set forth in SEQ ID NO: 4.

9. The method of claim 8, wherein the vector is a lentivirus, a gamma retrovirus, or an adeno-associated virus.

10. The viral vector of claim 5, wherein the viral vector is a lentiviral vector, a gamma-retroviral vector, or an adeno-associated viral vector.

* * * * *

SEQUENCE LISTING

```
<160> NUMBER OF SEQ ID NOS: 11

<210> SEQ ID NO 1
<211> LENGTH: 3972
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1354)..(3972)

<400> SEQUENCE: 1
gagtaattca tacaaaagga ctcgcccctg ccttggggaa tcccagggac cgtcgttaaa      60
ctcccactaa cgtagaaccc agagatcgct gcgttcccgc ccctcaccc gcccgctctc     120 gtcatcactg aggtggagaa gagcatgcgt gaggctccgg tgcccgtcag tgggcagagc     180
gcacatcgcc cacagtcccc gagaagttgg ggggaggggt cggcaattga accggtgcct     240
agagaaggtg gcgcggggta aactgggaaa gtgatgtcgt gtactggctc cgcctttttc     300
ccgagggtgg gggagaaccg tatataagtg cagtagtcgc cgtgaacgtt cttttcgca     360 acgggtttgc cgccagaaca caggtaagtg ccgtgtgtgg ttcccgcggg cctggcctct     420
ttacgggtta tggcccttgc gtgccttgaa ttacttccac gccctggct gcagtacgtg     480 attcttgatc ccgagcttcg ggttggaagt gggtgggaga gttcgaggcc ttgcgcttaa     540 ggagccct cgcctcgtgc ttgagttgag gcctggcttg ggcgctgggg ccgccgcgtg     600
cgaatctggt ggcaccttcg cgcctgtctc gctgctttcg ataagtctct agccatttaa     660 aattttttgat gacctgctgc gacgcttttt ttctggcaag atagtcttgt aaatgcgggc     720
caagatctgc acactggtat ttcggttttt ggggccgcgg gcggcgacgg ggcccgtgcg     780
tcccagcgca catgttcggc gaggcgggc ctgcgagcgc ggccaccgag aatcggacgg     840
gggtagtctc aagctggccg gcctgctctg gtgcctggcc tcgcgccgcc gtgtatcgcc     900
ccgccctggg cggcaaggct ggcccggtcg gcaccagttg cgtgagcgga aagatggccg     960
cttcccggcc ctgctgcagg gagctcaaaa tggaggacgg ggcgctcggg agagcgggcg    1020
ggtgagtcac ccacacaaag gaaaagggcc tttccgtcct cagccgtcgc ttcatgtgac    1080
tccacggagt accgggcgcc gtccaggcac ctcgattagt tctcgagctt ttggagtacg    1140
tcgtctttag gttggggga ggggttttat gcgatggagt ttccccacac tgagtgggtg    1200
gagactgaag ttaggccagc ttggcacttg atgtaattct ccttggaatt tgccctttt    1260 gagtttggat cttggttcat tctcaagcct cagacagtgg ttcaaagttt ttttcttcca    1320
tttcaggtgt cgtgattcga attcgccgcc acc atg gcc tta cca gtg acc gcc    1374
                                    Met Ala Leu Pro Val Thr Ala
                                    1               5 ttg ctc ctg ccg ctg gcc ttg ctc ctc cac gcc gcc agg ccg cag ctg       1422
Leu Leu Leu Pro Leu Ala Leu Leu Leu His Ala Ala Arg Pro Gln Leu
        10                  15                  20 caa gag tct ggc cct gga ctg gtc aag cct agc gag aca ctg agc ctg       1470
Gln Glu Ser Gly Pro Gly Leu Val Lys Pro Ser Glu Thr Leu Ser Leu
    25                  30                  35
```

-continued

| | | |
|---|---|---|
| acc tgt acc gtg tcc ggc ttt agc ctg aca agc tac ggc gtg gac tgg<br>Thr Cys Thr Val Ser Gly Phe Ser Leu Thr Ser Tyr Gly Val Asp Trp<br>40              45                  50                  55 | 1518 |
| gtc cga cag cct cct gga aaa ggc ctg gaa tgg atc ggc gtt atc tgg<br>Val Arg Gln Pro Pro Gly Lys Gly Leu Glu Trp Ile Gly Val Ile Trp<br>                60                  65                  70 | 1566 |
| ggc gga ggc agc acc aac tac aac agc gcc ctg atg agc cgg ctg acc<br>Gly Gly Gly Ser Thr Asn Tyr Asn Ser Ala Leu Met Ser Arg Leu Thr<br>            75                  80                  85 | 1614 |
| atc agc aag gac aac agc aag agc cag gtg tcc ctg aag ctg agc agc<br>Ile Ser Lys Asp Asn Ser Lys Ser Gln Val Ser Leu Lys Leu Ser Ser<br>        90                  95                  100 | 1662 |
| gtg aca gcc gct gat acc gcc gtg tac tac tgt gcc aag cac gag gtg<br>Val Thr Ala Ala Asp Thr Ala Val Tyr Tyr Cys Ala Lys His Glu Val<br>105                  110                  115 | 1710 |
| ctg aga ggc tac gcc ctg gat tat tgg ggc cag ggc aca ctg gtc aca<br>Leu Arg Gly Tyr Ala Leu Asp Tyr Trp Gly Gln Gly Thr Leu Val Thr<br>120                  125                  130                  135 | 1758 |
| gtg tct agc gga ggc gga gga agt ggt ggc gga gga tca ggc ggt ggt<br>Val Ser Ser Gly Gly Gly Gly Ser Gly Gly Gly Gly Ser Gly Gly Gly<br>                140                  145                  150 | 1806 |
| gga tct ctg aca cag tct ccc gct aca ctg tct ctg agc cct ggc gaa<br>Gly Ser Leu Thr Gln Ser Pro Ala Thr Leu Ser Leu Ser Pro Gly Glu<br>            155                  160                  165 | 1854 |
| aga gcc aca ctg agc tgt tct gcc tct cct agc gtg tcc tac atg cac<br>Arg Ala Thr Leu Ser Cys Ser Ala Ser Pro Ser Val Ser Tyr Met His<br>        170                  175                  180 | 1902 |
| tgg tat cag cag aag ccc gga cag gcc cct aga ctg ctg atc tac gac<br>Trp Tyr Gln Gln Lys Pro Gly Gln Ala Pro Arg Leu Leu Ile Tyr Asp<br>    185                  190                  195 | 1950 |
| acc tac aag ctg gcc tct ggc atc ccc gcc aga ttt tct ggc tct ggc<br>Thr Tyr Lys Leu Ala Ser Gly Ile Pro Ala Arg Phe Ser Gly Ser Gly<br>200                  205                  210                  215 | 1998 |
| agc ggc acc gat ttc acc ctg acc ata agc agc ctg gaa cct gag gac<br>Ser Gly Thr Asp Phe Thr Leu Thr Ile Ser Ser Leu Glu Pro Glu Asp<br>                220                  225                  230 | 2046 |
| ttc gct gtc tac tac tgc ttc caa ggc agc ggc ttc cct ctg aca ttt<br>Phe Ala Val Tyr Tyr Cys Phe Gln Gly Ser Gly Phe Pro Leu Thr Phe<br>            235                  240                  245 | 2094 |
| gga cag ggc acc aag gtg gaa atc aag acc act acc cca gca ccg agg<br>Gly Gln Gly Thr Lys Val Glu Ile Lys Thr Thr Thr Pro Ala Pro Arg<br>        250                  255                  260 | 2142 |
| cca ccc acc ccg gct cct acc atc gcc tcc cag cct ctg tcc ctg cgt<br>Pro Pro Thr Pro Ala Pro Thr Ile Ala Ser Gln Pro Leu Ser Leu Arg<br>    265                  270                  275 | 2190 |
| ccg gag gca tgt aga ccc gca gct ggt ggg gcc gtg cat acc cgg ggt<br>Pro Glu Ala Cys Arg Pro Ala Ala Gly Gly Ala Val His Thr Arg Gly<br>280                  285                  290                  295 | 2238 |
| ctt gac ttc gcc tgc gat atc tac att tgg gcc cct ctg gct ggt act<br>Leu Asp Phe Ala Cys Asp Ile Tyr Ile Trp Ala Pro Leu Ala Gly Thr<br>                300                  305                  310 | 2286 |
| tgc ggg gtc ctg ctg ctt tca ctc gtg atc act ctt tac tgt atc tac<br>Cys Gly Val Leu Leu Leu Ser Leu Val Ile Thr Leu Tyr Cys Ile Tyr<br>            315                  320                  325 | 2334 |
| att tgg gcc cct ctg gct ggt act tgc ggg gtc ctg ctg ctt tca ctc<br>Ile Trp Ala Pro Leu Ala Gly Thr Cys Gly Val Leu Leu Leu Ser Leu<br>        330                  335                  340 | 2382 |
| gtg atc act ctt tac tgt aag cgc ggt cgg aag aag ctg ctg tac atc<br>Val Ile Thr Leu Tyr Cys Lys Arg Gly Arg Lys Lys Leu Leu Tyr Ile<br>345                  350                  355 | 2430 |

-continued

| | | |
|---|---|---|
| ttt aag caa ccc ttc atg agg cct gtg cag act act caa gag gag gac<br>Phe Lys Gln Pro Phe Met Arg Pro Val Gln Thr Thr Gln Glu Glu Asp<br>360               365                 370                 375 | 2478 | |
| ggc tgt tca tgc cgg ttc cca gag gag gag gaa ggc ggc tgc gaa ctg<br>Gly Cys Ser Cys Arg Phe Pro Glu Glu Glu Glu Gly Gly Cys Glu Leu<br>                 380                 385                 390 | 2526 | |
| cgc gtg aaa ttc agc cgc agc gca gat gct cca gcc tac aag cag ggg<br>Arg Val Lys Phe Ser Arg Ser Ala Asp Ala Pro Ala Tyr Lys Gln Gly<br>             395                 400                 405 | 2574 | |
| cag aac cag ctc tac aac gaa ctc aat ctt ggt cgg aga gag gag tac<br>Gln Asn Gln Leu Tyr Asn Glu Leu Asn Leu Gly Arg Arg Glu Glu Tyr<br>410               415                 420 | 2622 | |
| gac gtg ctg gac aag cgg aga gga cgg gac cca gaa atg ggc ggg aag<br>Asp Val Leu Asp Lys Arg Arg Gly Arg Asp Pro Glu Met Gly Gly Lys<br>             425                 430                 435 | 2670 | |
| ccg cgc aga aag aat ccc caa gag ggc ctg tac aac gag ctc caa aag<br>Pro Arg Arg Lys Asn Pro Gln Glu Gly Leu Tyr Asn Glu Leu Gln Lys<br>440               445                 450                 455 | 2718 | |
| gat aag atg gca gaa gcc tat agc gag att ggt atg aaa ggg gaa cgc<br>Asp Lys Met Ala Glu Ala Tyr Ser Glu Ile Gly Met Lys Gly Glu Arg<br>                 460                 465                 470 | 2766 | |
| aga aga ggc aaa ggc cac gac gga ctg tac cag gga ctc agc acc gcc<br>Arg Arg Gly Lys Gly His Asp Gly Leu Tyr Gln Gly Leu Ser Thr Ala<br>             475                 480                 485 | 2814 | |
| acc aag gac acc tat gac gct ctt cac atg cag gcc ctg ccg cct cgg<br>Thr Lys Asp Thr Tyr Asp Ala Leu His Met Gln Ala Leu Pro Pro Arg<br>490               495                 500 | 2862 | |
| gag ggc aga ggc agc ctg ctg aca tgt ggc gac gtg gaa gag aac cct<br>Glu Gly Arg Gly Ser Leu Leu Thr Cys Gly Asp Val Glu Glu Asn Pro<br>             505                 510                 515 | 2910 | |
| ggc ccc atg tgg ctg cag agc ctg ctc ttg ggc act gtg gcc tgc<br>Gly Pro Met Trp Leu Gln Ser Leu Leu Leu Gly Thr Val Ala Cys<br>520               525                 530                 535 | 2958 | |
| agc atc tct cgc aaa gtg tgt aac gga ata ggt att ggt gaa ttt aaa<br>Ser Ile Ser Arg Lys Val Cys Asn Gly Ile Gly Ile Gly Glu Phe Lys<br>                 540                 545                 550 | 3006 | |
| gac tca ctc tcc ata aat gct acg aat att aaa cac ttc aaa aac tgc<br>Asp Ser Leu Ser Ile Asn Ala Thr Asn Ile Lys His Phe Lys Asn Cys<br>             555                 560                 565 | 3054 | |
| acc tcc atc agt ggc gat ctc cac atc ctg ccg gtg gca ttt agg ggt<br>Thr Ser Ile Ser Gly Asp Leu His Ile Leu Pro Val Ala Phe Arg Gly<br>570               575                 580 | 3102 | |
| gac tcc ttc aca cat act cct cct ctg gat cca cag gaa ctg gat att<br>Asp Ser Phe Thr His Thr Pro Pro Leu Asp Pro Gln Glu Leu Asp Ile<br>585               590                 595 | 3150 | |
| ctg aaa acc gta aag gaa atc aca ggg ttt ttg ctg att cag gct tgg<br>Leu Lys Thr Val Lys Glu Ile Thr Gly Phe Leu Leu Ile Gln Ala Trp<br>600               605                 610                 615 | 3198 | |
| cct gaa aac agg acg gac ctc cat gcc ttt gag aac cta gaa atc ata<br>Pro Glu Asn Arg Thr Asp Leu His Ala Phe Glu Asn Leu Glu Ile Ile<br>                 620                 625                 630 | 3246 | |
| cgc ggc agg acc aag caa cat ggt cag ttt tct ctt gca gtc gtc agc<br>Arg Gly Arg Thr Lys Gln His Gly Gln Phe Ser Leu Ala Val Val Ser<br>             635                 640                 645 | 3294 | |
| ctg aac ata aca tcc ttg gga tta cgc tcc ctc aag gag ata agt gat<br>Leu Asn Ile Thr Ser Leu Gly Leu Arg Ser Leu Lys Glu Ile Ser Asp<br>650               655                 660 | 3342 | |
| gga gat gtg ata att tca gga aac aaa aat ttg tgc tat gca aat aca<br>Gly Asp Val Ile Ile Ser Gly Asn Lys Asn Leu Cys Tyr Ala Asn Thr | 3390 | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 665 |     |     |     |     | 670 |     |     |     |     | 675 |     |     |      |
| ata | aac | tgg | aaa | aaa | ctg | ttt | ggg | acc | tcc | ggt | cag | aaa | acc | aaa | att | 3438 |
| Ile | Asn | Trp | Lys | Lys | Leu | Phe | Gly | Thr | Ser | Gly | Gln | Lys | Thr | Lys | Ile |      |
| 680 |     |     |     |     | 685 |     |     |     |     | 690 |     |     |     |     | 695 |      |
| ata | agc | aac | aga | ggt | gaa | aac | agc | tgc | aag | gcc | aca | ggc | cag | gtc | tgc | 3486 |
| Ile | Ser | Asn | Arg | Gly | Glu | Asn | Ser | Cys | Lys | Ala | Thr | Gly | Gln | Val | Cys |      |
|     |     |     |     | 700 |     |     |     |     | 705 |     |     |     |     | 710 |     |      |
| cat | gcc | ttg | tgc | tcc | ccc | gag | ggc | tgc | tgg | ggc | ccg | gag | ccc | agg | gac | 3534 |
| His | Ala | Leu | Cys | Ser | Pro | Glu | Gly | Cys | Trp | Gly | Pro | Glu | Pro | Arg | Asp |      |
|     |     |     | 715 |     |     |     |     | 720 |     |     |     |     | 725 |     |     |      |
| tgc | gtc | tct | tgc | cgg | aat | gtc | agc | cga | ggc | agg | gaa | tgc | gtg | gac | aag | 3582 |
| Cys | Val | Ser | Cys | Arg | Asn | Val | Ser | Arg | Gly | Arg | Glu | Cys | Val | Asp | Lys |      |
|     |     | 730 |     |     |     |     | 735 |     |     |     |     | 740 |     |     |     |      |
| tgc | aac | ctt | ctg | gag | ggt | gag | cca | agg | gag | ttt | gtg | gag | aac | tct | gag | 3630 |
| Cys | Asn | Leu | Leu | Glu | Gly | Glu | Pro | Arg | Glu | Phe | Val | Glu | Asn | Ser | Glu |      |
| 745 |     |     |     |     | 750 |     |     |     |     | 755 |     |     |     |     |     |      |
| tgc | ata | cag | tgc | cac | cca | gag | tgc | ctg | cct | cag | gcc | atg | aac | atc | acc | 3678 |
| Cys | Ile | Gln | Cys | His | Pro | Glu | Cys | Leu | Pro | Gln | Ala | Met | Asn | Ile | Thr |      |
| 760 |     |     |     |     | 765 |     |     |     |     | 770 |     |     |     |     | 775 |      |
| tgc | aca | gga | cgg | gga | cca | gac | aac | tgt | atc | cag | tgt | gcc | cac | tac | att | 3726 |
| Cys | Thr | Gly | Arg | Gly | Pro | Asp | Asn | Cys | Ile | Gln | Cys | Ala | His | Tyr | Ile |      |
|     |     |     |     | 780 |     |     |     |     | 785 |     |     |     |     | 790 |     |      |
| gac | ggc | ccc | cac | tgc | gtc | aag | acc | tgc | ccg | gca | gga | gtc | atg | gga | gaa | 3774 |
| Asp | Gly | Pro | His | Cys | Val | Lys | Thr | Cys | Pro | Ala | Gly | Val | Met | Gly | Glu |      |
|     |     |     | 795 |     |     |     |     | 800 |     |     |     |     | 805 |     |     |      |
| aac | aac | acc | ctg | gtc | tgg | aag | tac | gca | gac | gcc | ggc | cat | gtg | tgc | cac | 3822 |
| Asn | Asn | Thr | Leu | Val | Trp | Lys | Tyr | Ala | Asp | Ala | Gly | His | Val | Cys | His |      |
|     |     + 810 |     |     |     |     | 815 |     |     |     |     | 820 |     |     |     |      |
| ctg | tgc | cat | cca | aac | tgc | acc | tac | gga | tgc | act | ggg | cca | ggt | ctt | gaa | 3870 |
| Leu | Cys | His | Pro | Asn | Cys | Thr | Tyr | Gly | Cys | Thr | Gly | Pro | Gly | Leu | Glu |      |
| 825 |     |     |     |     | 830 |     |     |     |     | 835 |     |     |     |     |     |      |
| ggc | tgt | cca | acg | aat | ggg | cct | aag | atc | ccg | tcc | atc | gcc | act | ggg | atg | 3918 |
| Gly | Cys | Pro | Thr | Asn | Gly | Pro | Lys | Ile | Pro | Ser | Ile | Ala | Thr | Gly | Met |      |
| 840 |     |     |     |     | 845 |     |     |     |     | 850 |     |     |     |     | 855 |      |
| gtg | ggg | gcc | ctc | ctc | ttg | ctg | ctg | gtg | gtg | gcc | ctg | ggg | atc | ggc | ctc | 3966 |
| Val | Gly | Ala | Leu | Leu | Leu | Leu | Leu | Val | Val | Ala | Leu | Gly | Ile | Gly | Leu |      |
|     |     |     |     | 860 |     |     |     |     | 865 |     |     |     |     | 870 |     |      |
| ttc | atg |     |     |     |     |     |     |     |     |     |     |     |     |     |     | 3972 |
| Phe | Met |     |     |     |     |     |     |     |     |     |     |     |     |     |     |      |

<210> SEQ ID NO 2
<211> LENGTH: 873
<212> TYPE: PRT
<213> ORGANISM: Artificial Sequence
<220> FEATURE:
<223> OTHER INFORMATION: Synthetic Construct

<400> SEQUENCE: 2

Met Ala Leu Pro Val Thr Ala Leu Leu Leu Pro Leu Ala Leu Leu Leu
1               5                   10                  15

His Ala Ala Arg Pro Gln Leu Gln Glu Ser Gly Pro Gly Leu Val Lys
                20                  25                  30

Pro Ser Glu Thr Leu Ser Leu Thr Cys Thr Val Ser Gly Phe Ser Leu
            35                  40                  45

Thr Ser Tyr Gly Val Asp Trp Val Arg Gln Pro Pro Gly Lys Gly Leu
        50                  55                  60

Glu Trp Ile Gly Val Ile Trp Gly Gly Gly Ser Thr Asn Tyr Asn Ser
65                  70                  75                  80

Ala Leu Met Ser Arg Leu Thr Ile Ser Lys Asp Asn Ser Lys Ser Gln

-continued

```
                    85                  90                  95
Val Ser Leu Lys Leu Ser Ser Val Thr Ala Asp Thr Ala Val Tyr
                100                 105                 110
Tyr Cys Ala Lys His Glu Val Leu Arg Gly Tyr Ala Leu Asp Tyr Trp
                115                 120                 125
Gly Gln Gly Thr Leu Val Thr Val Ser Ser Gly Gly Gly Ser Gly
        130                 135                 140
Gly Gly Gly Ser Gly Gly Gly Ser Leu Thr Gln Ser Pro Ala Thr
145                 150                 155                 160
Leu Ser Leu Ser Pro Gly Glu Arg Ala Thr Leu Ser Cys Ser Ala Ser
                165                 170                 175
Pro Ser Val Ser Tyr Met His Trp Tyr Gln Gln Lys Pro Gly Gln Ala
                180                 185                 190
Pro Arg Leu Leu Ile Tyr Asp Thr Tyr Lys Leu Ala Ser Gly Ile Pro
                195                 200                 205
Ala Arg Phe Ser Gly Ser Gly Ser Gly Thr Asp Phe Thr Leu Thr Ile
                210                 215                 220
Ser Ser Leu Glu Pro Glu Asp Phe Ala Val Tyr Tyr Cys Phe Gln Gly
225                 230                 235                 240
Ser Gly Phe Pro Leu Thr Phe Gly Gln Gly Thr Lys Val Glu Ile Lys
                245                 250                 255
Thr Thr Thr Pro Ala Pro Arg Pro Pro Thr Pro Ala Pro Thr Ile Ala
                260                 265                 270
Ser Gln Pro Leu Ser Leu Arg Pro Glu Ala Cys Arg Pro Ala Ala Gly
                275                 280                 285
Gly Ala Val His Thr Arg Gly Leu Asp Phe Ala Cys Asp Ile Tyr Ile
                290                 295                 300
Trp Ala Pro Leu Ala Gly Thr Cys Gly Val Leu Leu Leu Ser Leu Val
305                 310                 315                 320
Ile Thr Leu Tyr Cys Ile Tyr Ile Trp Ala Pro Leu Ala Gly Thr Cys
                325                 330                 335
Gly Val Leu Leu Leu Ser Leu Val Ile Thr Leu Tyr Cys Lys Arg Gly
                340                 345                 350
Arg Lys Lys Leu Leu Tyr Ile Phe Lys Gln Pro Phe Met Arg Pro Val
                355                 360                 365
Gln Thr Thr Gln Glu Glu Asp Gly Cys Ser Cys Arg Phe Pro Glu Glu
        370                 375                 380
Glu Glu Gly Gly Cys Glu Leu Arg Val Lys Phe Ser Arg Ser Ala Asp
385                 390                 395                 400
Ala Pro Ala Tyr Lys Gln Gly Gln Asn Gln Leu Tyr Asn Glu Leu Asn
                405                 410                 415
Leu Gly Arg Arg Glu Glu Tyr Asp Val Leu Asp Lys Arg Arg Gly Arg
                420                 425                 430
Asp Pro Glu Met Gly Gly Lys Pro Arg Arg Lys Asn Pro Gln Glu Gly
                435                 440                 445
Leu Tyr Asn Glu Leu Gln Lys Asp Lys Met Ala Glu Ala Tyr Ser Glu
        450                 455                 460
Ile Gly Met Lys Gly Glu Arg Arg Arg Gly Lys Gly His Asp Gly Leu
465                 470                 475                 480
Tyr Gln Gly Leu Ser Thr Ala Thr Lys Asp Thr Tyr Asp Ala Leu His
                485                 490                 495
Met Gln Ala Leu Pro Pro Arg Glu Gly Arg Gly Ser Leu Leu Thr Cys
                500                 505                 510
```

Gly Asp Val Glu Glu Asn Pro Gly Pro Met Trp Leu Gln Ser Leu Leu
            515                 520                 525

Leu Leu Gly Thr Val Ala Cys Ser Ile Ser Arg Lys Val Cys Asn Gly
        530                 535                 540

Ile Gly Ile Gly Glu Phe Lys Asp Ser Leu Ser Ile Asn Ala Thr Asn
545                 550                 555                 560

Ile Lys His Phe Lys Asn Cys Thr Ser Ile Ser Gly Asp Leu His Ile
                565                 570                 575

Leu Pro Val Ala Phe Arg Gly Asp Ser Phe Thr His Thr Pro Pro Leu
            580                 585                 590

Asp Pro Gln Glu Leu Asp Ile Leu Lys Thr Val Lys Glu Ile Thr Gly
        595                 600                 605

Phe Leu Leu Ile Gln Ala Trp Pro Glu Asn Arg Thr Asp Leu His Ala
    610                 615                 620

Phe Glu Asn Leu Glu Ile Ile Arg Gly Arg Thr Lys Gln His Gly Gln
625                 630                 635                 640

Phe Ser Leu Ala Val Val Ser Leu Asn Ile Thr Ser Leu Gly Leu Arg
                645                 650                 655

Ser Leu Lys Glu Ile Ser Asp Gly Asp Val Ile Ile Ser Gly Asn Lys
            660                 665                 670

Asn Leu Cys Tyr Ala Asn Thr Ile Asn Trp Lys Lys Leu Phe Gly Thr
        675                 680                 685

Ser Gly Gln Lys Thr Lys Ile Ile Ser Asn Arg Gly Glu Asn Ser Cys
    690                 695                 700

Lys Ala Thr Gly Gln Val Cys His Ala Leu Cys Ser Pro Glu Gly Cys
705                 710                 715                 720

Trp Gly Pro Glu Pro Arg Asp Cys Val Ser Cys Arg Asn Val Ser Arg
                725                 730                 735

Gly Arg Glu Cys Val Asp Lys Cys Asn Leu Leu Glu Gly Glu Pro Arg
            740                 745                 750

Glu Phe Val Glu Asn Ser Glu Cys Ile Gln Cys His Pro Glu Cys Leu
        755                 760                 765

Pro Gln Ala Met Asn Ile Thr Cys Thr Gly Arg Gly Pro Asp Asn Cys
    770                 775                 780

Ile Gln Cys Ala His Tyr Ile Asp Gly Pro His Cys Val Lys Thr Cys
785                 790                 795                 800

Pro Ala Gly Val Met Gly Glu Asn Asn Thr Leu Val Trp Lys Tyr Ala
                805                 810                 815

Asp Ala Gly His Val Cys His Leu Cys His Pro Asn Cys Thr Tyr Gly
            820                 825                 830

Cys Thr Gly Pro Gly Leu Glu Gly Cys Pro Thr Asn Gly Pro Lys Ile
        835                 840                 845

Pro Ser Ile Ala Thr Gly Met Val Gly Ala Leu Leu Leu Leu Leu Val
    850                 855                 860

Val Ala Leu Gly Ile Gly Leu Phe Met
865                 870

<210> SEQ ID NO 3
<211> LENGTH: 235
<212> TYPE: PRT
<213> ORGANISM: Artificial Sequence
<220> FEATURE:
<223> OTHER INFORMATION: single chain Fv

<400> SEQUENCE: 3

```
Gln Leu Gln Glu Ser Gly Pro Gly Leu Val Lys Pro Ser Glu Thr Leu
1               5                   10                  15

Ser Leu Thr Cys Thr Val Ser Gly Phe Ser Leu Thr Ser Tyr Gly Val
            20                  25                  30

Asp Trp Val Arg Gln Pro Pro Gly Lys Gly Leu Glu Trp Ile Gly Val
        35                  40                  45

Ile Trp Gly Gly Ser Thr Asn Tyr Asn Ser Ala Leu Met Ser Arg
50                  55                  60

Leu Thr Ile Ser Lys Asp Asn Ser Lys Ser Gln Val Ser Leu Lys Leu
65                  70                  75                  80

Ser Ser Val Thr Ala Ala Asp Thr Ala Val Tyr Tyr Cys Ala Lys His
                85                  90                  95

Glu Val Leu Arg Gly Tyr Ala Leu Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Leu Thr Gln Ser Pro Ala Thr Leu Ser Leu Ser Pro
    130                 135                 140

Gly Glu Arg Ala Thr Leu Ser Cys Ser Ala Ser Pro Ser Val Ser Tyr
145                 150                 155                 160

Met His Trp Tyr Gln Gln Lys Pro Gly Gln Ala Pro Arg Leu Leu Ile
                165                 170                 175

Tyr Asp Thr Tyr Lys Leu Ala Ser Gly Ile Pro Ala Arg Phe Ser Gly
            180                 185                 190

Ser Gly Ser Gly Thr Asp Phe Thr Leu Thr Ile Ser Ser Leu Glu Pro
        195                 200                 205

Glu Asp Phe Ala Val Tyr Tyr Cys Phe Gln Gly Ser Gly Phe Pro Leu
    210                 215                 220

Thr Phe Gly Gln Gly Thr Lys Val Glu Ile Lys
225                 230                 235

<210> SEQ ID NO 4
<211> LENGTH: 490
<212> TYPE: PRT
<213> ORGANISM: Artificial Sequence
<220> FEATURE:
<223> OTHER INFORMATION: Synthetic polypeptide

<400> SEQUENCE: 4

Met Ala Leu Pro Val Thr Ala Leu Leu Leu Pro Leu Ala Leu Leu Leu
1               5                   10                  15

His Ala Ala Arg Pro Gln Leu Gln Glu Ser Gly Pro Gly Leu Val Lys
            20                  25                  30

Pro Ser Glu Thr Leu Ser Leu Thr Cys Thr Val Ser Gly Phe Ser Leu
        35                  40                  45

Thr Ser Tyr Gly Val Asp Trp Val Arg Gln Pro Pro Gly Lys Gly Leu
    50                  55                  60

Glu Trp Ile Gly Val Ile Trp Gly Gly Ser Thr Asn Tyr Asn Ser
65                  70                  75                  80

Ala Leu Met Ser Arg Leu Thr Ile Ser Lys Asp Asn Ser Lys Ser Gln
                85                  90                  95

Val Ser Leu Lys Leu Ser Ser Val Thr Ala Ala Asp Thr Ala Val Tyr
            100                 105                 110

Tyr Cys Ala Lys His Glu Val Leu Arg Gly Tyr Ala Leu Asp Tyr Trp
        115                 120                 125
```

Gly Gln Gly Thr Leu Val Thr Val Ser Ser Gly Gly Gly Ser Gly
         130                 135                 140

Gly Gly Gly Ser Gly Gly Gly Ser Leu Thr Gln Ser Pro Ala Thr
145                 150                 155                 160

Leu Ser Leu Ser Pro Gly Glu Arg Ala Thr Leu Ser Cys Ser Ala Ser
             165                 170                 175

Pro Ser Val Ser Tyr Met His Trp Tyr Gln Gln Lys Pro Gly Gln Ala
                 180                 185                 190

Pro Arg Leu Leu Ile Tyr Asp Thr Tyr Lys Leu Ala Ser Gly Ile Pro
         195                 200                 205

Ala Arg Phe Ser Gly Ser Gly Ser Gly Thr Asp Phe Thr Leu Thr Ile
210                 215                 220

Ser Ser Leu Glu Pro Glu Asp Phe Ala Val Tyr Tyr Cys Phe Gln Gly
225                 230                 235                 240

Ser Gly Phe Pro Leu Thr Phe Gly Gln Gly Thr Lys Val Glu Ile Lys
                 245                 250                 255

Thr Thr Thr Pro Ala Pro Arg Pro Pro Thr Pro Ala Pro Thr Ile Ala
                 260                 265                 270

Ser Gln Pro Leu Ser Leu Arg Pro Glu Ala Cys Arg Pro Ala Ala Gly
         275                 280                 285

Gly Ala Val His Thr Arg Gly Leu Asp Phe Ala Cys Asp Lys Arg Gly
290                 295                 300

Arg Lys Lys Leu Leu Tyr Ile Phe Lys Gln Pro Phe Met Arg Pro Val
305                 310                 315                 320

Gln Thr Thr Gln Glu Glu Asp Gly Cys Ser Cys Arg Phe Pro Glu Glu
                 325                 330                 335

Glu Glu Gly Gly Cys Glu Leu Arg Val Lys Phe Ser Arg Ser Ala Asp
                 340                 345                 350

Ala Pro Ala Tyr Lys Gln Gly Gln Asn Gln Leu Tyr Asn Glu Leu Asn
         355                 360                 365

Leu Gly Arg Arg Glu Glu Tyr Asp Val Leu Asp Lys Arg Arg Gly Arg
370                 375                 380

Asp Pro Glu Met Gly Gly Lys Pro Arg Arg Lys Asn Pro Gln Glu Gly
385                 390                 395                 400

Leu Tyr Asn Glu Leu Gln Lys Asp Lys Met Ala Glu Ala Tyr Ser Glu
                 405                 410                 415

Ile Gly Met Lys Gly Glu Arg Arg Arg Gly Lys Gly His Asp Gly Leu
                 420                 425                 430

Tyr Gln Gly Leu Ser Thr Ala Thr Lys Asp Thr Tyr Asp Ala Leu His
         435                 440                 445

Met Gln Ala Leu Pro Pro Arg Glu Gly Arg Gly Ser Leu Leu Thr Cys
450                 455                 460

Gly Asp Val Glu Glu Asn Pro Gly Pro Met Trp Leu Gln Ser Leu Leu
465                 470                 475                 480

Leu Leu Gly Thr Val Ala Cys Ser Ile Ser
                 485                 490

<210> SEQ ID NO 5
<211> LENGTH: 352
<212> TYPE: PRT
<213> ORGANISM: Artificial Sequence
<220> FEATURE:
<223> OTHER INFORMATION: Synthetic ploypeptide

<400> SEQUENCE: 5

```
Met Trp Leu Gln Ser Leu Leu Leu Gly Thr Val Ala Cys Ser Ile
1               5                   10                  15

Ser Arg Lys Val Cys Asn Gly Ile Gly Ile Gly Glu Phe Lys Asp Ser
            20                  25                  30

Leu Ser Ile Asn Ala Thr Asn Ile Lys His Phe Lys Asn Cys Thr Ser
        35                  40                  45

Ile Ser Gly Asp Leu His Ile Leu Pro Val Ala Phe Arg Gly Asp Ser
    50                  55                  60

Phe Thr His Thr Pro Leu Asp Pro Gln Glu Leu Asp Ile Leu Lys
65                  70                  75                  80

Thr Val Lys Glu Ile Thr Gly Phe Leu Leu Ile Gln Ala Trp Pro Glu
                85                  90                  95

Asn Arg Thr Asp Leu His Ala Phe Glu Asn Leu Glu Ile Ile Arg Gly
            100                 105                 110

Arg Thr Lys Gln His Gly Gln Phe Ser Leu Ala Val Val Ser Leu Asn
            115                 120                 125

Ile Thr Ser Leu Gly Leu Arg Ser Leu Lys Glu Ile Ser Asp Gly Asp
        130                 135                 140

Val Ile Ile Ser Gly Asn Lys Asn Leu Cys Tyr Ala Asn Thr Ile Asn
145                 150                 155                 160

Trp Lys Lys Leu Phe Gly Thr Ser Gly Gln Lys Thr Lys Ile Ile Ser
                165                 170                 175

Asn Arg Gly Glu Asn Ser Cys Lys Ala Thr Gly Gln Val Cys His Ala
            180                 185                 190

Leu Cys Ser Pro Glu Gly Cys Trp Gly Pro Glu Pro Arg Asp Cys Val
        195                 200                 205

Ser Cys Arg Asn Val Ser Arg Gly Arg Glu Cys Val Asp Lys Cys Asn
    210                 215                 220

Leu Leu Glu Gly Glu Pro Arg Glu Phe Val Glu Asn Ser Glu Cys Ile
225                 230                 235                 240

Gln Cys His Pro Glu Cys Leu Pro Gln Ala Met Asn Ile Thr Cys Thr
                245                 250                 255

Gly Arg Gly Pro Asp Asn Cys Ile Gln Cys Ala His Tyr Ile Asp Gly
            260                 265                 270

Pro His Cys Val Lys Thr Cys Pro Ala Gly Val Met Gly Glu Asn Asn
        275                 280                 285

Thr Leu Val Trp Lys Tyr Ala Asp Ala Gly His Val Cys His Leu Cys
    290                 295                 300

His Pro Asn Cys Thr Tyr Gly Cys Thr Gly Pro Gly Leu Glu Gly Cys
305                 310                 315                 320

Pro Thr Asn Gly Pro Lys Ile Pro Ser Ile Ala Thr Gly Met Val Gly
                325                 330                 335

Ala Leu Leu Leu Leu Leu Val Val Ala Leu Gly Ile Gly Leu Phe Met
            340                 345                 350

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
tgacagccgc ctagcatttc                                            20
```

```
<210> SEQ ID NO 7
<211> LENGTH: 24
<212> TYPE: DNA
<213> ORGANISM: Artificial Sequence
<220> FEATURE:
<223> OTHER INFORMATION: Synthetic primer

<400> SEQUENCE: 7
gctcgatatc agcagttctt gaag                                        24

<210> SEQ ID NO 8
<211> LENGTH: 22
<212> TYPE: DNA
<213> ORGANISM: Artificial Sequence
<220> FEATURE:
<223> OTHER INFORMATION: Synthetic probe

<400> SEQUENCE: 8
cacgtggccc gagagctgca tc                                          22

<210> SEQ ID NO 9
<211> LENGTH: 22
<212> TYPE: DNA
<213> ORGANISM: Artificial Sequence
<220> FEATURE:
<223> OTHER INFORMATION: Synthetic primer

<400> SEQUENCE: 9
gctgtcatct cttgtgggct gt                                          22

<210> SEQ ID NO 10
<211> LENGTH: 21
<212> TYPE: DNA
<213> ORGANISM: Artificial Sequence
<220> FEATURE:
<223> OTHER INFORMATION: Synthetic primer

<400> SEQUENCE: 10
actcatggga gctgctggtt c                                           21

<210> SEQ ID NO 11
<211> LENGTH: 26
<212> TYPE: DNA
<213> ORGANISM: Artificial Sequence
<220> FEATURE:
<223> OTHER INFORMATION: Synthetic probe

<400> SEQUENCE: 11
cctgtcatgc ccacacaaat ctctcc                                      26
```